(12) United States Patent
Katsevich et al.

(10) Patent No.: US 9,042,626 B1
(45) Date of Patent: May 26, 2015

(54) SYSTEM AND METHOD FOR HYBRID LOCAL TOMOGRAPHY IMAGE RECONSTRUCTION

(71) Applicants: University of Central Florida Research Foundation, Inc., Orlando, FL (US); iTomography Corporation, Barker, TX (US)

(72) Inventors: Alexander Katsevich, Oviedo, FL (US); Michael Frenkel, Barker, TX (US)

(73) Assignees: University of Central Florida Research Foundation, Inc., Orlando, FL (US); iTomography Corporation, Barker, TX (US)

( * ) Notice: Subject to any disclaimer, the term of this patent is extended or adjusted under 35 U.S.C. 154(b) by 0 days.

(21) Appl. No.: 14/557,046

(22) Filed: Dec. 1, 2014

Related U.S. Application Data

(63) Continuation-in-part of application No. 14/080,099, filed on Nov. 14, 2013, now Pat. No. 8,929,637, which is a continuation-in-part of application No. 13/722,383, filed on Dec. 20, 2012, now Pat. No. 8,611,631.

(51) Int. Cl.
| | |
|---|---|
| G06K 9/00 | (2006.01) |
| G06T 11/00 | (2006.01) |
| A61B 6/03 | (2006.01) |
| A61B 6/00 | (2006.01) |
| G06T 5/00 | (2006.01) |
| G06T 5/20 | (2006.01) |

(52) U.S. Cl.
CPC ............ *G06T 11/005* (2013.01); *A61B 6/032* (2013.01); *A61B 6/4085* (2013.01); *A61B 6/469* (2013.01); *A61B 6/5217* (2013.01); *G06T 5/003* (2013.01); *G06T 5/20* (2013.01); *G06T 11/006* (2013.01); *G06T 2207/10081* (2013.01); *G06T 2207/20024* (2013.01); *G06T 2207/20192* (2013.01); *G06T 2207/30004* (2013.01); *G06T 2211/424* (2013.01); *G06T 2211/421* (2013.01)

(58) Field of Classification Search
None
See application file for complete search history.

(56) References Cited

U.S. PATENT DOCUMENTS

| | | | |
|---|---|---|---|
| 5,539,800 | A | 7/1996 | Katsevich et al. |
| 5,550,892 | A | 8/1996 | Katsevich et al. |
| 5,717,211 | A | 2/1998 | Katsevich |
| 5,881,123 | A | 3/1999 | Tam |
| 7,590,216 | B2 | 9/2009 | Katsevich |

OTHER PUBLICATIONS

Faridani et al., Introduction to local tomography.Contemp. Math., 278, Amer. Math. Soc, 2001, pp. 29-47.
Katsevich et al., Local Tomography: a New Concept in Computed Tompgraphy Reconstructions, 2011. pp. 1-4.
Katsevich, Cone beam local tomography, SIAM Journal on Applied Mathematics. 1999. vol. 59 (No. 6): 2224-2246.

(Continued)

*Primary Examiner* — Atiba O Fitzpatrick
(74) *Attorney, Agent, or Firm* — Molly L. Sauter; Smith & Hopen, P.A.

(57) ABSTRACT

Methods, processes and systems of image reconstruction utilizing a hybrid local tomography (HLT) methodology for reconstructing internal body images in medical applications, and the like. The system and method of the present invention provides an image with emphasized edges, and the image provides estimations of the attenuation coefficient inside the object being scanned.

39 Claims, 10 Drawing Sheets

(56) References Cited

OTHER PUBLICATIONS

Katsevich. Improved cone beam local tomography, Inverse Problems. 2006. vol. 22: 627-643.

Louis and Maass, Contour reconstruction in 3-D X-ray CT, IEEE Transactions on Medical Imaging. 1993. vol. 12 (No. 4): 764-769.

Moscariello et al., Coronary CT Angiography: Image Quality, Diagnostic Accuracy, and Potential for Radiation Does Reduction Using a Novel Iterative Image Reconstruction Technique—Comparison with Traditional Filtered Back Projection, Euro. Radiol. 2011. vol. 21: 2130-2138.

Park et al. Automatic Tube Potential Selection with Tube Current Modulation (APSCM) in coronary CT angiography: Comparison of image quality and radiation dose with conventional body mass index-based protocol. Journal of Cardiovascular Computed Tomography .2012. vol. 6: 184-190.

Raff. Radiation dose from coronary CT angiography: Five years of progress. Journal of Cardiovascular Computed Tomography .2010. vol. 4: 365-374.

Sato et al., Effect of radiation dose and adaptive statistical iterative reconstruction on image quality of pulmonary computed tomography. Jpn J Radiol. 2012. vol. 30:146-153.

Chen, Local volume reconstruction from width-truncated cone-beam projections by convolution backprojection, Optical Engineering. 2008. vol. 47 (Issue 1): 1-10.

Kim et al., Accelerating X-ray CT ordered subsets image reconstruction with Nesterov's first-order methods. Proceedings of the 12th International Meeting on Fully Three-Dimensional Image Reconstruction in Radiology and Nuclear Medicine. 2013: 22-25.

SYSTEM AND METHOD FOR HYBRID LOCAL TOMOGRAPHY IMAGE RECONSTRUCTION

STATEMENT OF GOVERNMENT INTEREST

This invention was made with government support under NSF (National Science Foundation) award DMS-0806304, and DMS-1211164. The government has certain rights in this invention.

CROSS-REFERENCE TO RELATED APPLICATIONS

This application claims priority to co-pending U.S. patent application Ser. No. 14/080,099, entitled "Variable Filter Length Local Tomography", filed Nov. 14, 2013, which claims priority to U.S. patent application Ser. No. 13/722,383, entitled "Variable Filter Length Local Tomography", filed Dec. 20, 2012, the contents of which are herein incorporated in their entirety.

FIELD OF INVENTION

This invention relates to image reconstruction and in particular to methods and systems of Computed Tomography (CT) enhanced image reconstruction using a new Hybrid Local Tomography (HLT) method, which is based on Local Tomography (LT) and conventional tomography techniques for reconstructing internal body images in medical applications, and the like.

BACKGROUND OF THE INVENTION

Recognition of the dangers of ionizing radiation has become more focused over time. The recent focus on reducing dose became more urgent with the advent of cardiac Computed Tomography (CT). See for example, Raff, G. L., Radiation dose from coronary CT angiography: Five years of progress. Journal of Cardiovascular Computed Tomography (2010) 4, 365-374. These are inherently high dose procedures. Attempts to reduce dose include adaptive iterative reconstructions and modulating the tube potential during the scan.

See for example, Sato, J., M. Akahane, S. Inano et al., "Effect of radiation dose and adaptive statistical iterative reconstruction on image quality of pulmonary computed tomography", Jpn J Radiol (2012) 30:146-153; and Park, Y J Kim, J W Lee, et al. "Automatic Tube Potential Selection with Tube Current Modulation (APSCM) in coronary CT angiography: Comparison of image quality and radiation dose with conventional body mass index-based protocol", Journal of Cardiovascular Computed Tomography (2012) 6, 184-190.

Suppose one is interested in reconstructing a region of interest (ROI) inside a patient. In a particular case, the ROI may be in the cardiac region. Conventional (also known as global) reconstruction requires that the entire cross-section of the patient be irradiated. This means that during the scan one has to transmit x-rays through parts of the patient located far from the ROI. In the past 10-15 years, a group of algorithms called Local Tomography (LT) was developed. See, for example, Ramm A., and A. Katsevich, "The Radon transform and local tomography", CRC Press, Boca Raton, Fla., 1996, and Katsevich, A., "Improved cone beam local tomography", Inverse Problems 22 (2006), 627-643.

The main idea of LT is based on transmitting only those X-rays through the patient that intersect the ROI inside the patient. The X-rays that do not pass through the ROI are blocked from reaching the patient, which results in a reduction of the dose of a CT scan.

Conventional CT reconstructs the distribution $\mu$ of the x-ray attenuation coefficient inside the object being scanned. Normally, $\mu$ is measured in Hounsfield units. LT computes not $\mu$, but $B\mu$, where B is some operator that enhances singularities of $\mu$ (e.g., edges). Thus, the information about the actual values of $\mu$ inside the ROI is not recovered.

In two dimensions, the main mathematical basis for LT is provided by the following two formulas (A) and (B):

$$f_\Lambda = \frac{1}{4\pi} \int_0^{2\pi} g''(\alpha, \alpha \cdot x) d\alpha, \qquad (A)$$

$$f_\Lambda = F^{-1}(|\xi|\tilde{f}(\xi)), \qquad (B)$$

where $\tilde{f}$ is the Fourier transform of f; $F^{-1}$ is the inverse Fourier transform; and g represents the CT data.

The fact that the first formula, A, contains only one integral demonstrates that LT reconstruction is local. The presence of the growing factor $|\xi|$ in the second formula proves that LT enhances edges. The useful property of LT, which also follows from the second equation, is that it preserves all geometric features inside the ROI. In other words, the sharp features of $\mu$ (e.g., location of edges) coincide with sharp features of $B\mu$. See for example: Ramm A., and A. Katsevich, "The Radon transform and local tomography", CRC Press, Boca Raton, Fla., 1996; and Faridani, A., K. Buglione, P. Huabsomboon, et al., "Introduction to local tomography, Radon transforms and tomography", Contemp. Math., 278, Amer. Math. Soc, 2001, pp. 29-47. Thus, in some sense, LT is close to the gradient of the true image f.

In the cone beam setting (e.g., in helical scanning), the situation is more complicated. The reason is that B may add sharp features that are not present in $\mu$. See for example, Katsevich, A., "Cone beam local tomography", SIAM Journal on Applied Mathematics (1999), 2224-2246. This manifests itself as artifacts. However, it was shown by one of the subject inventors that by choosing an appropriate direction of filtering, one can significantly reduce the strength of the artifacts and potentially reduce dose. See for example, Katsevich, A., "Improved cone beam local tomography", Inverse Problems 22 (2006), 627-643.

In classical cone beam LT the convolution kernel is very short, because it is equivalent to computing some kind of derivative on the detector. See for example, Louis A. K., and P. Maass, "Contour reconstruction in 3-D X-ray CT, IEEE Transactions on Medical Imaging", 12 (1993), 764-769 and Katsevich, A., "Improved cone beam local tomography", Inverse Problems 22 (2006), 627-643.

A main disadvantage of LT is that LT images look different from conventional CT images, which may result in a loss of diagnostic information. Since LT emphasizes edges and does not reconstruct $\mu$ in Hounsfield units (HU) it is sometimes hard to differentiate between tissue types and even see the presence of the X-ray contrast agent in the blood.

Thus, a need exists in the art for a system and method for the reconstruction of images having emphasized edges in which the reconstructed image also includes information about the actual values of the attenuation coefficient inside the object being scanned.

SUMMARY OF INVENTION

The present invention provides methods, processes and systems for image reconstruction of internal body images in medical applications, and the like, which allows for both differentiation between tissue types and for the detection of the presence of the X-ray contrast agent in the blood.

An objective of one embodiment of the present invention is to provide methods, processes and systems for image reconstruction of internal body images in medical applications, and the like, that uses less radiation (less x-rays) to target body areas for image reconstruction than prior art techniques.

An objective of another embodiment of the present invention is to provide methods, processes and systems for reconstruction of images of object's interior in medical applications, and the like, that provides estimates of the values of the attenuation coefficient inside the object being scanned.

In one embodiment, the present invention provides a method for reconstructing an image of a region of interest (ROI) of an object, the image including a distribution of the attenuation coefficient of the ROI, which includes, scanning an object to collect cone-beam (CB) projection data of the object, the CB projection data provided to a computer by at least one detector. The method further includes, reconstructing a conventional image of the ROI using the CB projection data, the conventional image of the ROI comprising the distribution of the attenuation coefficient of the ROI, and reconstructing an LT image of the ROI using the CB projection data, the LT image of the ROI comprising emphasized edges of the ROI. After the LT image and the conventional image of the ROI have been reconstructed, the method further includes, computing a high-pass filtered LT image of the ROI from the LT image of the ROI, identifying a first balancing constant or function and computing a summation of the conventional image of the ROI and a product of the first balancing constant or function and the high-pass filtered LT image of the ROI to reconstruct a first image of the ROI of the object, the first image of the ROI including the values of the attenuation coefficient of the ROI.

In an additional embodiment, the method of the present invention may further include, computing a low-pass filtered conventional image of the ROI from the conventional image of the ROI, identifying a second balancing constant or function and computing a summation of the conventional image of the ROI and a product of the second balancing constant or function and the high-pass filtered LT image of the ROI to reconstruct a second image of the ROI of the object, the second image including the values of the attenuation coefficient of the ROI.

The first image of the ROI and the second image of the ROI may then be compared to identify the better quality image resulting from the method of the present invention.

In an additional embodiment, the present invention provides a system, including a scanner and a computer, configured for performing the method of the present invention as described.

The present invention provides a system and method for the reconstruction of images having emphasized edges, in which the reconstructed image also include information about the actual values of the distribution of the attenuation coefficient inside the object being scanned.

The following detailed description of the presently preferred embodiments, which are illustrated schematically in the accompanying drawings.

DETAILED DESCRIPTION OF THE PREFERRED EMBODIMENT

Figure 1:
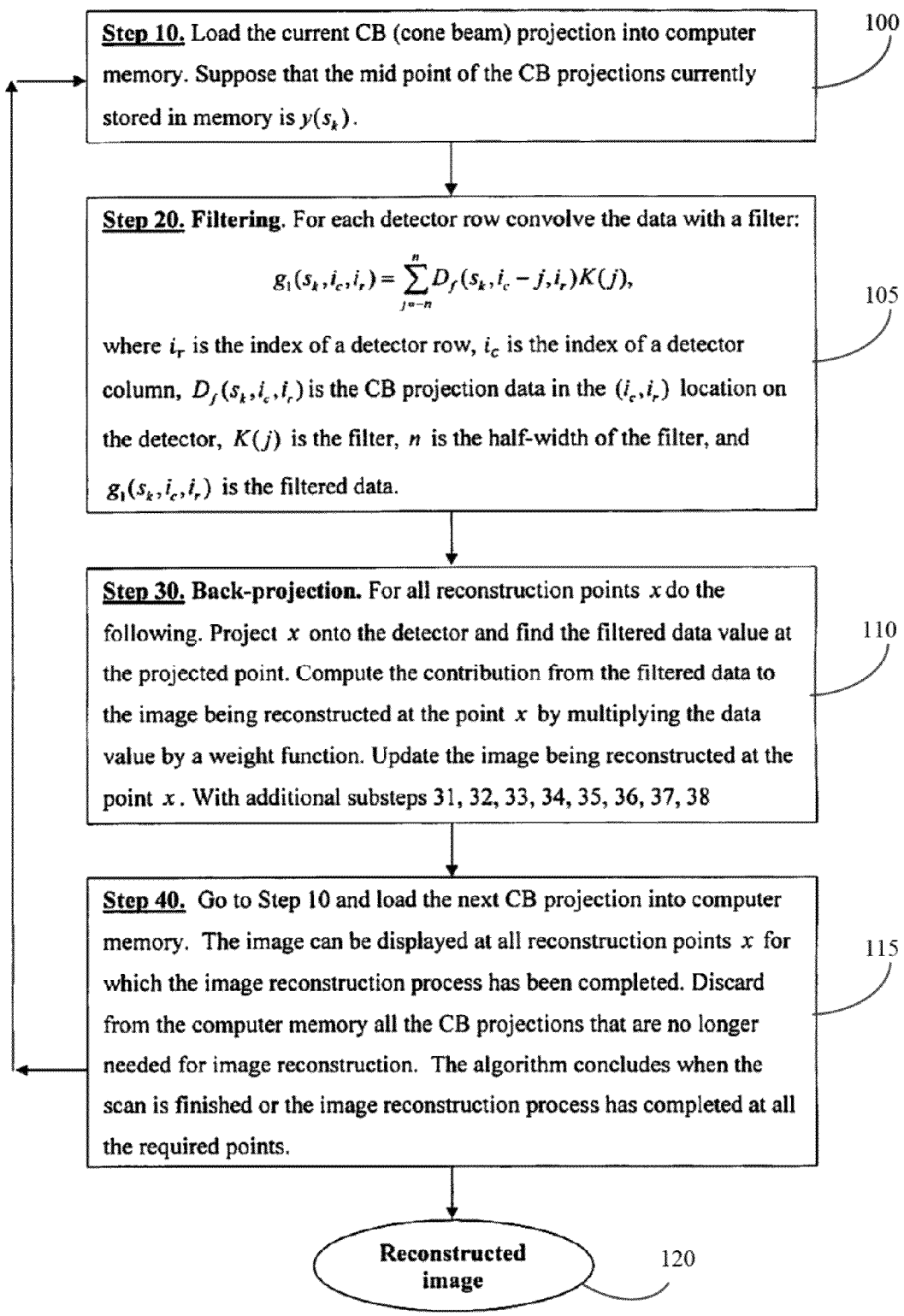
FIG. 1 is a flowchart illustrating the steps for reconstruction using variable filter length LT in accordance with an embodiment of the present invention

It is to be understood that the invention is not limited in its applications to the details of the particular arrangements shown since the invention is capable of other embodiments. Also, the terminology used herein is for the purpose of description and not of limitation.

One of the subject inventors, Dr. Alexander Katsevich, has patented image reconstruction that includes LT. See for example, U.S. Pat. Nos. 5,539,800; 5,550,892; 5,717,211 all to Katsevich, which in their entirety are all incorporated by reference. Additionally, Dr. Katsevich has patented an invention in cone beam LT. See for example, U.S. Pat. No. 7,590,216 to Katsevich, which in its' entirety is also incorporated by reference. The prior patents include but are not limited to collecting cone beam (CB) projection data from at least one detector, in order to reconstruct images of an object.

The subject invention can use the same equipment described in these patents with a novel computer run algorithm which is described below.

For the subject invention, the mathematical description of the algorithm is given by the following formula:

$$f(x) = \int w(s,x) \int D_f(s, u(s,x) - u, v) K(u) du ds, \quad (1.1)$$

where s is a parameter along the source trajectory, $f_1$ is the image to be reconstructed, x is a reconstruction point, K(u) is a reconstruction kernel, w(s,x) is a weight function, u and v are row- and column-coordinates on the detector, respectively, u(s,x) and v(s,x) are the row- and column-coordinates of the projection of a reconstruction point x on the detector corresponding to the source position y(s), and $D_f$ is the cone-beam data. In discrete form, equation (1.1) can be written as follows:

$$f_1(x) = \sum_k w(s_k, x) \sum_{j=-n}^{n} D_f(s_k, u(s_k, x) - u_j, v) K(u_j) \Delta u \Delta s, \quad (1.2)$$

where n is the half-length of the filter, and $\Delta u$ and $\Delta s$ are the step-sizes along the u and s variables, respectively.

The LT is quite flexible and a wide variety of weight functions and reconstruction kernels is possible. For example, we can choose $$K(j) = \begin{cases} 0, & \text{if } |j| \text{ is even and } j \neq 0 \text{ or } |j| > n; \\ 1/j^2, & \text{if } |j| \text{ is odd and } |j| \leq n; \\ -2\sum_{i=1}^{L} (1/i^2), & j = 0. \end{cases} \quad (1.3)$$

An example of a weight function is as follows:

$$w(s,x) = (R - (x_1 y_1(s) + x_2 y_2(s))/R)^{-1},$$

where R is the radius of the helix, $x_1$, $x_2$ are the in-plane coordinates of a reconstruction point, and $y_1(s)$, $y_2(s)$ are the in-plane coordinates of the current source position y(s).

The interval of integration in (1.1) and, correspondingly, the range of summation in (1.2), may depend on the specifics of the image reconstruction problem. In the case of cardiac CT when image reconstruction at a certain cardiac phase is required, the weight function w(s,x) will include additional factors that go to zero farther away from the desired phase. More generally, the weight function may include factors that go to zero near the detector boundary to reduce data truncation artifacts. The cone-beam data $D_f(s,u,v)$ are measured by the detector at a discrete set of points $u = \Delta u i_c$, $v = \Delta v i_r$, where $i_r$ denotes the index of a detector row, and $i_c$ denotes the index of a detector column. Thus, in what follows, for simplicity the detector data are denoted $D_f(s, i_c, i_r)$.

As stated, equation (1.1) does not involve weighting of the CB data $D_f(s,u,v)$ prior to convolution. Other embodiments of the algorithm are possible, in which the CB data are multiplied by a weight factor prior to the convolution. Regardless of whether the CB data are weighted prior to convolution or not, in both cases we say that the CB data are filtered.

The filter K(j) of the present invention is similar to the filter described by equation (6) in Z. Chen, Local volume reconstruction from width-truncated cone-beam projections by convolution backprojection, Optical Engineering, volume 47 (2008), issue 1. The main difference between the two filters is the value of K(0). As is known, the filter needs to satisfy the equation $$\sum_{j=-\infty}^{\infty} K(j) = 0. \quad (1.4)$$

The filter in equation (1.3) satisfies equation (1.4). In an effort to make reconstruction from truncated data as close to conventional reconstruction as possible, in paper Z. Chen, Local volume reconstruction from width-truncated cone-beam projections by convolution backprojection, Optical Engineering, volume 47 (2008), issue 1, the author truncates the conventional filter at some length and keeps all other filter values the same. Consequently, as the filter length n becomes increasingly small, the filter in Z. Chen, Local volume reconstruction from width-truncated cone-beam projections by convolution backprojection, Optical Engineering, volume 47 (2008), issue 1, violates equation (1.4) more strongly and the corresponding reconstructions become increasingly worse as confirmed by the following quote from the paper: "... a short kernel incurs a large error, as revealed in FIG. 2b".

Conceptually, the main difference between the approach in Z. Chen, Local volume reconstruction from width-truncated cone-beam projections by convolution backprojection, Optical Engineering, volume 47 (2008), issue 1, and the approach in the present invention is that the former attempts to make reconstruction from truncated data as close to conventional reconstruction as possible, which, in particular, necessitates the use of data extrapolation. In the present invention the goal is to come up with an image that only looks qualitatively similar to conventional reconstruction. In particular, the algorithm of the present invention can be used with non-truncated data as well.

In a first embodiment of the present invention, a novel variable filter length LT method is described for the reconstruction of an image of an object. FIG. 1 is a flowchart illustrating the steps for reconstruction using variable length tomography in accordance with this first embodiment of the present invention. With reference to FIG. 1, at step 100 the current CB (cone beam) projection $D_f(s,u,v)$ is collected and loaded into computer memory. It is assumed that this CB projection corresponds to the source position $y(s_k)$. The detector surface corresponding to the x-ray source located at $y(s_k)$ is denoted $DP(s_k)$. Filtering is performed at step 105, wherein for each detector row convolve the data with a filter. Let $i_r$ be the index of a detector row, $i_c$ be the index of a detector column, and let $D_f(s_k, i_c, i_r)$ be the CB projection data in the $(i_c, i_r)$ location on the detector. We use the following equation (cf. equation (1.2)):

$$g_1(s_k, i_c, i_r) = \sum_{j=-n}^{n} D_f(s_k, i_c - j, i_r) K(j), \quad (1.5)$$

where K(j) is the filter, n is the half-width of the filter, and $g_1(s_k, i_c, i_r)$ is the filtered data.

By itself, the filtering step is well known in the field and can be implemented, for example, as shown and described in U.S. Pat. No. 5,881,123 to Tam, which is incorporated by reference. Alternative implementation of the convolution can be based on the Fast Fourier Transform (FFT).

Following the filtering of the data 105, backprojection of the filtered data is performed 110, wherein a reconstruction point x, is fixed which represents a point inside the patient where it is required to reconstruct the image. Next, the projection $\hat{x}$ of x onto the detector surface $DP(s_k)$ Let $(i_c^x, i_r^x)$ is found to be the row- and column-coordinates of $\hat{x}$ on the detector. If $\hat{x}$ projects onto the detector, the said filtered CB data affects the image at x and additional steps are performed. If $\hat{x}$ projects outside the detector, then the said filtered CB data are not used for image reconstruction at x. In this case, another reconstruction point is chosen and the reconstruction is restarted.

As previously stated, if $\hat{x}$ projects onto the detector, the filtered CB data affects the image at x, and additional steps are performed, which include identify the rows and columns on the detector that are close to the projection $\hat{x}$. This will give a few values of $g_1(s_k,i_c,i_r)$ for $(i_c,i_r)$ close to $(i_c^x,i_r^x)$. Following identification of the rows and columns, the method includes and interpolation estimate of the value of $g_1(s_0,i_c^x,i_r^x)$ from the said values of $g_1(s_0,i_c,i_r)$ for $(i_c,i_r)$ close to $(i_c^x,i_r^x)$ and a computation of the contribution from the filtered CB data to the image being reconstructed at the point x by multiplying $g_1(s_k,i_c^x,i_r^x)$ by a weight function $w(s_k,x)$. Next, the contribution to the image being reconstructed at the point x according to a pre-selected scheme (for example, the Trapezoidal scheme) for approximate evaluation of the integral in equation (1.1) according to (1.2). Following this step, a different reconstruction point is chosen, the next CB projection is loaded into computer memory 100 and the reconstruction of the images continues.

At 115, the image can be displayed at all reconstruction points x for which the image reconstruction process has been completed (that is, all the subsequent CB projections are not needed for reconstructing the image at those points). Discard from the computer memory all the CB projections that are not needed for image reconstruction at points where the image reconstruction process has not completed. The algorithm concludes when the scan is finished or the image reconstruction process has completed at all the required points.

Figure 2:
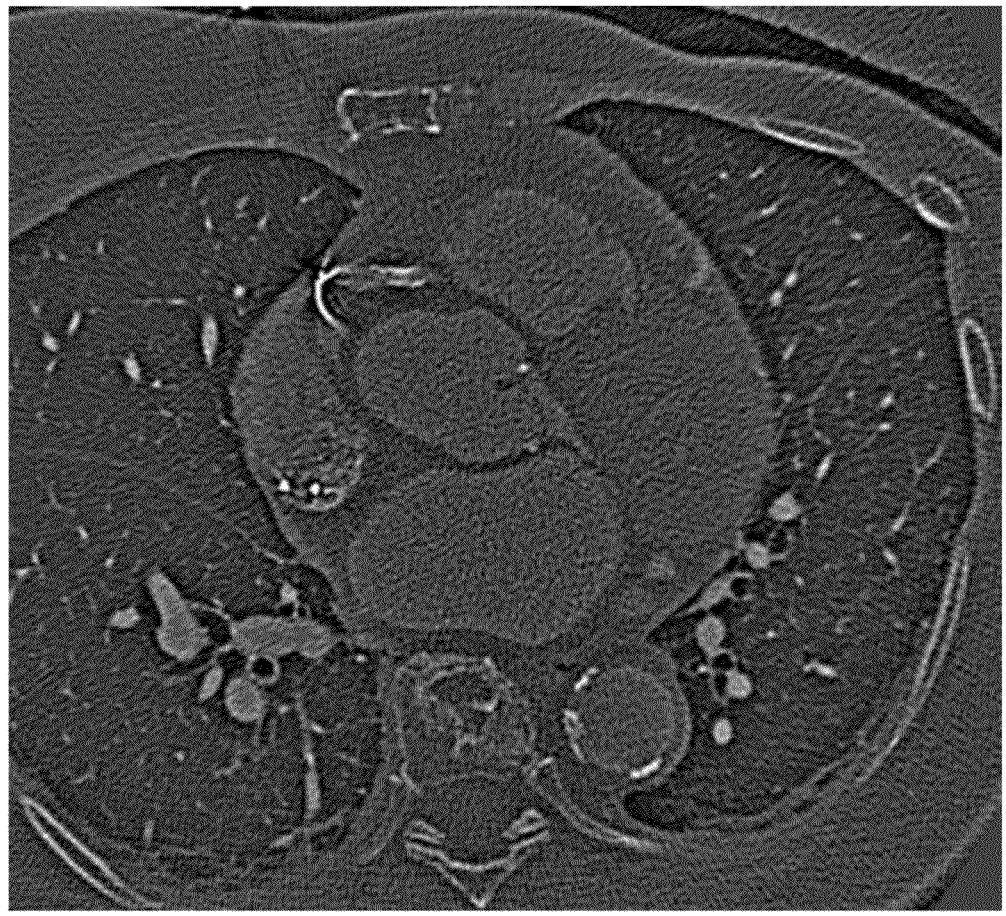
FIG. 2 is an illustration of image reconstruction using the prior art LT techniques.
Figure 3:
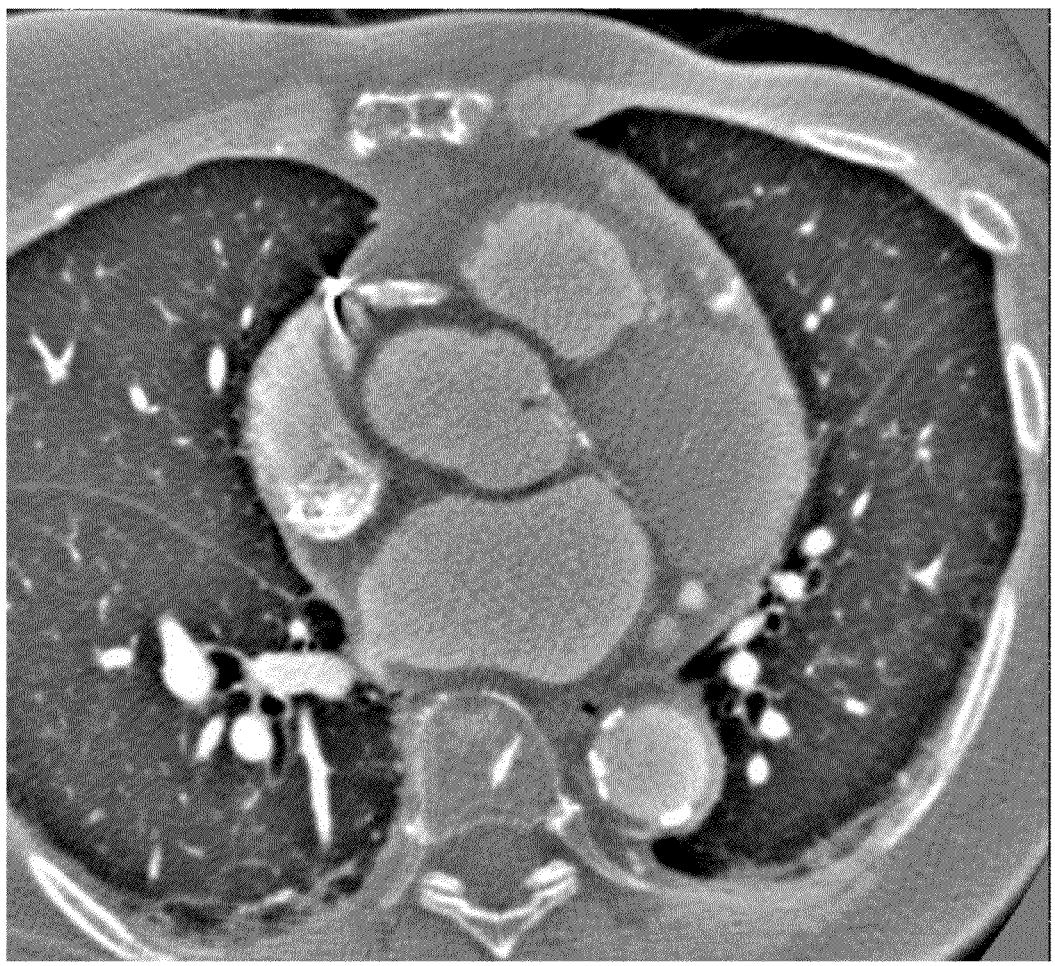
FIG. 3 is an illustration of image reconstruction using the invented variable filter length LT in accordance with an embodiment of the present invention.

FIG. 2 illustrates an image reconstruction in accordance with the prior art LT. For comparison, FIG. 3 illustrates an image reconstruction using the inventive variable filter length LT of the first embodiment of the present invention. It is clearly seen that the image in FIG. 3 is much more informative than that illustrated in FIG. 2. In FIG. 3, different tissue types can be easily differentiated and contrast media inside blood vessels is visible.

As is seen from the description of the methods steps illustrated in FIG. 1, the variable filter length LT algorithm of the first embodiment of the present invention is computationally efficient. It contains steps like filtering, backprojection, multiplication by a weight function, and the like. Most importantly, for each source position, the filtering on the detector is performed along a one-parametric family of curves. In contrast, the algorithms of prior art that reconstruct images from truncated data are generally computationally expensive in view of the extra computer power, time and memory needed. The invention can consist of minimal steps that do not require the extra computer power, time and memory needed. For example, filtered back projection is an example of an algorithm that only requires minimal extra steps in addition to filtering and backprojection to operate. The minimal steps can include but are not limited to multiplication of data (non-filtered and filtered) by a weight function, linear interpolation, smoothing, and the like. The variable filter length LT algorithm described in the first embodiment of the present invention does not include any iterative steps, filling in of the missing data, using wavelets, curvelets, and the like.

A study of image reconstruction using the novel variable filter length LT algorithm occurred at the Texas Medical Center in Houston. The first part of this study was retrospective analysis of patients comparing anatomy on selected slices of the coronary computed tomography angiogram (CCTA) with reconstructions using LT tomography at the same level (s). Subsequently, to test the feasibility of viewing anatomy that was comparable on the two types of reconstructions, other subjects who would consent were prospectively recruited from all patients that presented to the hospital CT scanner in whom a cardiac computed tomography angiogram was ordered by the referring physician.

Following patient consent, scans were obtained on a CB CT scanner utilizing helical scanning and dose modulated retrospective ECG gating. The contrast agent was utilized.

For all cases raw CT data was stripped of identifying information, assigned a study number, and transferred to an external hard drive for subsequent analysis by the variable filter length LT algorithm of the first embodiment of the present invention. In a parallel fashion the scanner raw CT data was processed and reconstructed in a routine manner and transferred to a CT visualization workstation for review and clinical reading and report by a radiologist or cardiologist responsible for the normal workflow. For the study, this reconstructed data was also stripped of patient identifiers and used for the study. Two experienced readers compared the variable filter length LT images and the conventional CT images for diagnostic accuracy, spatial resolution, and contrast resolution and an assessment of whether all lesions seen on the conventional CTA were identified by the variable filter length LT reconstructed images.

An estimate was made about the range of potential radiation dose savings based upon the individual geometry of the scan regions of interest.

Feedback from the two experienced readers from the Texas Medical Center showed that the variable filter length LT of the present invention provides excellent anatomical rendering, including differentiation of tissue types, and the contrast is clearly visible as well. These results show that the variable filter length LT of the first embodiment of the present invention has the potential to decrease radiation by ~50%.

Although the invention is primarily directed to image reconstruction of internal body images (of cardiac and other organs/body parts), the invention can be used in other applications. For example, the novel algorithm can be used for security screening and non-destructive evaluation of cargo at airports and shipping ports. The invention can be used for scanning small and large machine parts for defects. The invention can further be used in wood working applications to determine the location of knots and cracks.

The algorithm in accordance with the variable filter length LT embodiment of the invention reconstructs an image at a reconstruction point x using tomographic data corresponding to integrals along lines passing through a neighborhood of x. Therefore the algorithm is suitable for reconstructing a region of interest inside an object from truncated data. On the other hand, the algorithm can be used for reconstructing the entire object from non-truncated data since it can visualize certain features inside the object better than the traditional theoretically exact methods (iterative and non-iterative).

As discussed in the background of the invention, a main disadvantage of prior art LT techniques, including the variable filter length LT embodiment of the present invention, is that LT images look different from conventional (i.e., global) CT images, which may result in a loss of diagnostic information. While LT algorithms, such as the variable filter length LT method of the first embodiment of the present invention, provide edge-enhanced image reconstruction in CT and have the advantage of being very efficient by employing filtered-backprojection (FBP) techniques, a disadvantage of LT is that the attenuation coefficient $\mu$ in Hounsfield units (HU) is not reconstructed in LT. Since the true HU values are not reconstructed when LT techniques are employed, it is sometimes hard to differentiate between tissue types and even to see the presence of the X-ray contrast agent in the blood.

In accordance with an additional embodiment of the present invention, a system and method for the reconstruction of images having emphasized edges in which the reconstructed image also includes information about the actual values of the distribution of the attenuation coefficient $\mu$ inside the object is provided. The present invention proposes an additional embodiment in which a Hybrid Local Tomography (HLT) algorithm provides edge-enhanced reconstruction, while also providing fairly accurate HU values. The main idea of the proposed algorithm of this second embodiment, is the novel combination of a conventional reconstruction with an LT-based reconstruction.

In an exemplary embodiment of the HLT reconstruction method in accordance with the present invention, let $f_c(x)$ denote an image reconstructed by a conventional (i.e., exact or quasi-exact) algorithm. Such an algorithm can be based on, but not limited to, an iterative-based reconstruction algorithm or an FBP-reconstruction algorithm. Let $f_1(x)$ denote the reconstructed LT image, wherein $f_1(x)$ is computed using the formula (1.2), as previously presented. Following the LT theory, $f_1$ preserves and enhances all the edges (or features with high spatial frequency content) visible from the data in the object being scanned. On the other hand, the low-frequency features contained in $f_1$ carry little useful information regarding edges or sharp changes of the attenuation coefficient μ and may even create artifacts in LT-based images. Hence, it is proposed to remove or attenuate low frequency content from $f_1$. As such, let $\tilde{f}_1$ be the result of applying a high-pass filter to $f_1$ in the image domain:

$$\tilde{f}_1 = f_1 * \omega, \tag{1.6}$$

where ω is a high-pass filter, and the star (*) denotes convolution in the image domain.

A first hybrid reconstruction formula proposed is:

$$f_{h1} = f_c + c\tilde{f}_1 \tag{1.7}$$

where c>0 is some balancing constant or function.

In order to provide a higher quality image using $f_{h1}$, one needs to balance the frequency contents of $f_c$ and $\tilde{f}_1$, and the impact of c. The optimal value or shape of "c" can be determined using, for example, synthetic simulations and/or multiple case studies. In a particular embodiment, an expert opinion can be used to find the best value of "c". Since human bodies are rather similar, an optimal predetermined value of "c" is appropriate in many cases.

Various methods may be used to determine the optimal value or shape of "c" for reconstructing an HLT image. In one embodiment, "c" may be determined automatically, during the actual reconstruction of the images, by using a predetermined mathematical algorithm. In an additional embodiment, predetermined possible choices for "c" may be prepared prior to the actual reconstruction and a user will be responsible for selecting the best value of "c" for the particular application from the predetermined possible choices of "c". In this embodiment, it is envisioned that there will be different values of "c" for imaging of bones, heart, lungs, etc. In another embodiment, the value of "c" can be adjusted by the user during the actual reconstruction of the HLT images.

The frequency content (or, spectrum) of $f_c$ depends on the reconstruction algorithm. If $f_c$ is computed using an iterative algorithm, then the spectrum of $f_c$ depends on the strength of regularization, number of iterations, achieved convergence, number/type of basis functions used, etc. If $f_c$ is computed using an FBP-type algorithm, the spectrum of $f_c$ depends on data filtration, the reconstruction kernel, etc.

In this specific embodiment, since $f_1$ is computed using an FBP algorithm, the main factors affecting the spectrum of $\tilde{f}_1$ are data filtration, filter length L in (1.3), and the high-pass filter ω in (1.6).

In an additional embodiment, to reduce a possible misbalance of high-frequency data generated by both a conventional and an LT-based algorithm, an additional filtering step for $f_c$ proposed, in which:

$$\tilde{f}_c = f_c * \omega_2, \tag{1.8}$$

where $\omega_2$ is a low-pass filter kernel.

Following the additional filtering step, a second hybrid reconstruction formula is proposed, in which:

$$f_{h2} = \tilde{f}_c + c\tilde{f}_1 \tag{1.9}$$

The value of "c" in the second HLT reconstruction formula (1.9) may be the same value, or a different value, than the value of "c" used in the first HLT reconstruction formula (1.7).

Figure 4:
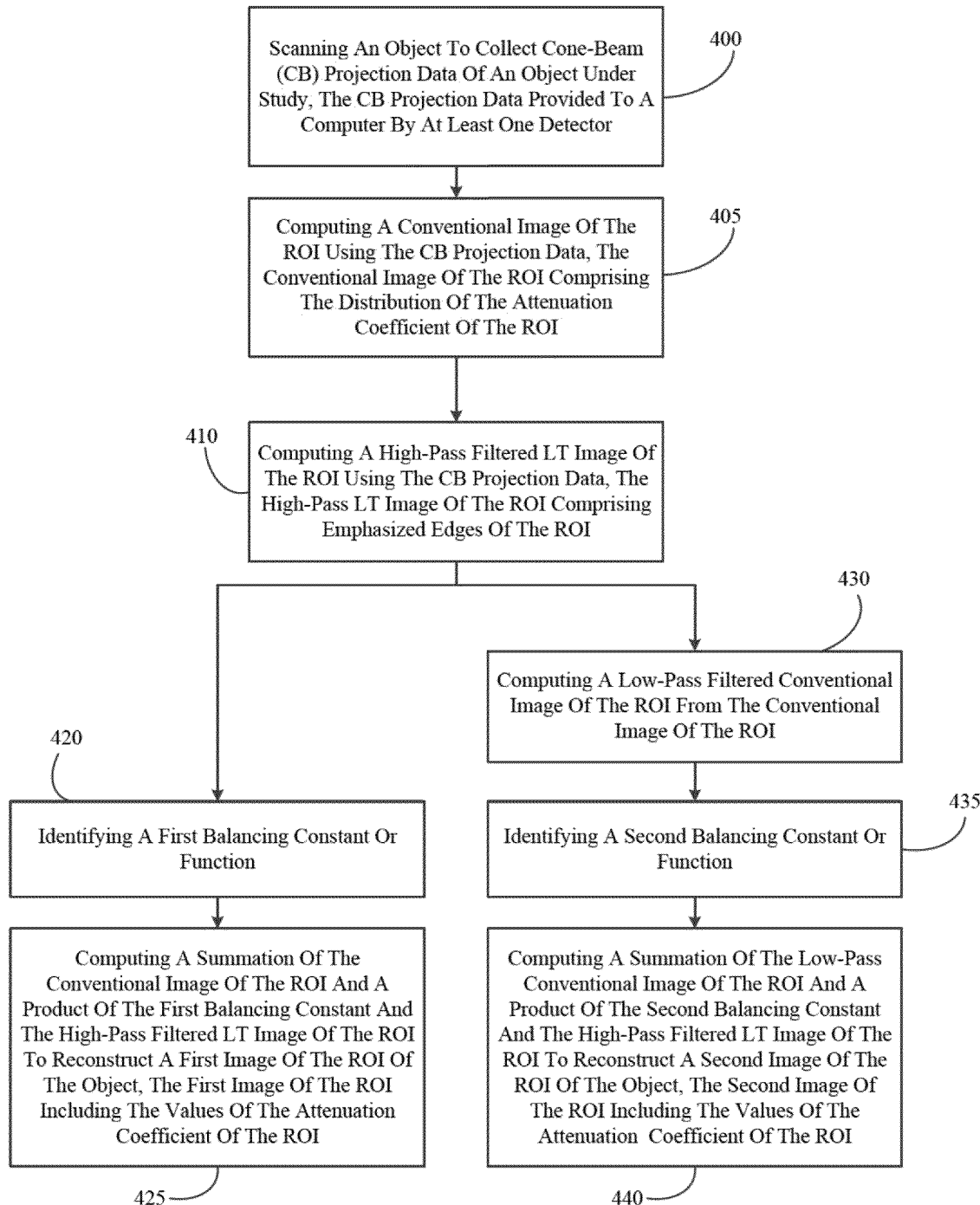
FIG. 4 is a flowchart illustrating the steps for Hybrid LT (HLT) image reconstruction method in accordance with an embodiment of the present invention.

With reference to FIG. 4, the method of the present invention includes, scanning an object to collect cone-beam (CB) projection data of the object under study (being scanned) and providing the CB projection data to a computer by at least one detector 400. After the CB projection data has been received by the computer, the method continues by computing a conventional image of the region of interest (ROI) using the CB projection data, wherein the conventional image of the ROI comprises the values of the attenuation coefficient of the ROI 405. The method further includes, computing an LT image of the ROI using the CB projection data, wherein the LT image of the ROI comprises emphasized edges of the ROI 410. In one embodiment, the high-pass filtered LT image may be computed in a single step. In an alternative embodiment, the high-pass filtered LT image may be computed by first reconstructing the LT image from the CB projection data and then filtering the reconstructed LT image using a high-pass filter to generate the high-pass filtered LT image. After the LT image and the conventional image of the ROI have been reconstructed, the method further includes, identifying a first balancing constant or function 420 and computing a summation of the conventional image of the ROI and a product of the first balancing constant or function and the high-pass filtered LT image of the ROI to reconstruct a first HLT image of the ROI of the object, the first HLT image of the ROI including the values of the attenuation coefficient of the ROI 425. The values of the attenuation coefficient included in the first image of the ROI generated by the HLT method of the present invention provides HU values that are close to the true values.

In an additional embodiment, the method of the present invention may further include, computing a low-pass filtered conventional image of the ROI from the conventional image of the ROI 430, identifying a second balancing constant or function 435 and computing a summation of the low-pass filtered conventional image of the ROI and a product of the second balancing constant or function and the high-pass filtered LT image of the ROI to reconstruct a second HLT image of the ROI of the object, the second HLT image including the values of the attenuation coefficient of the ROI 440. The values of the attenuation coefficient included in the second HLT image of the ROI generated by the hybrid LT method of the present invention provides HU values that are close to the true values. In one embodiment, the low-pass filtered conventional image may be computed in a single step. In an alternative embodiment, the low-pass filtered conventional image may be computed by first reconstructing the conventional image from the CB projection data and then filtering the reconstructed conventional image using a low-pass filter to generate the low-pass filtered conventional image.

The enhanced first HLT image and second HLT image of the ROI resulting from the method of the present invention may be provided as output and a comparison of the two images (volumes) may be performed to identify the highest quality HLT image of an object being scanned.

In an additional embodiment, the method of the present invention may include an additional data filtering step prior to reconstructing the conventional image and/or LT image of the ROI, wherein the filtering step includes performing raw CT data filtration to remove random and/or sensor noise. This pre-image reconstruction technique may be applied to the real raw CT data acquired by the CT scanner at any stage prior to the beginning of the image reconstruction step.

In a particular embodiment, the variable filter length LT method of the first embodiment of the present invention may be used for the reconstruction of the LT-based image of the ROI to be used in the HLT image reconstruction method embodiment of the present invention.

In another embodiment, post-reconstruction image enhancement may be performed in which additional iterative image enhancement of the first image and/or the second HLT image of the ROI may be performed using a regularization algorithm.

In an exemplary embodiment of the present invention, a first HLT image is reconstructed and the results of the $f_{h1}$ reconstruction from a simulated data set are presented in FIGS. 5-9. In this exemplary embodiment, the low-pass filtering step described by (1.8) to compute $f_c$ has been omitted.

Figure 7:
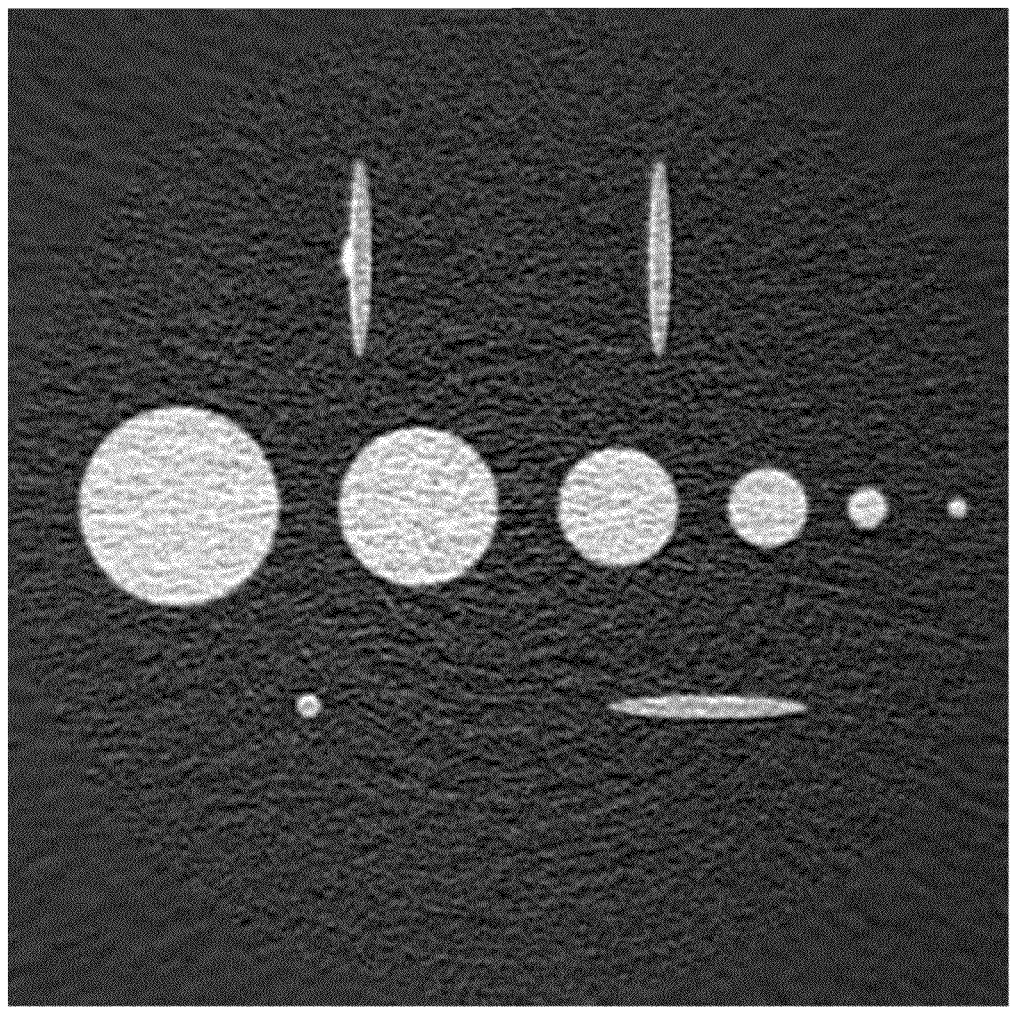
FIG. 7 is an illustration of the same slice as in FIG. 5 through the reconstructed volume of $f_{h1}$ resulting from the novel Hybrid Local Tomography (HLT) reconstruction in accordance with a conventional tomography algorithm and a LT algorithm in accordance with an embodiment of the present invention.
Figure 8:
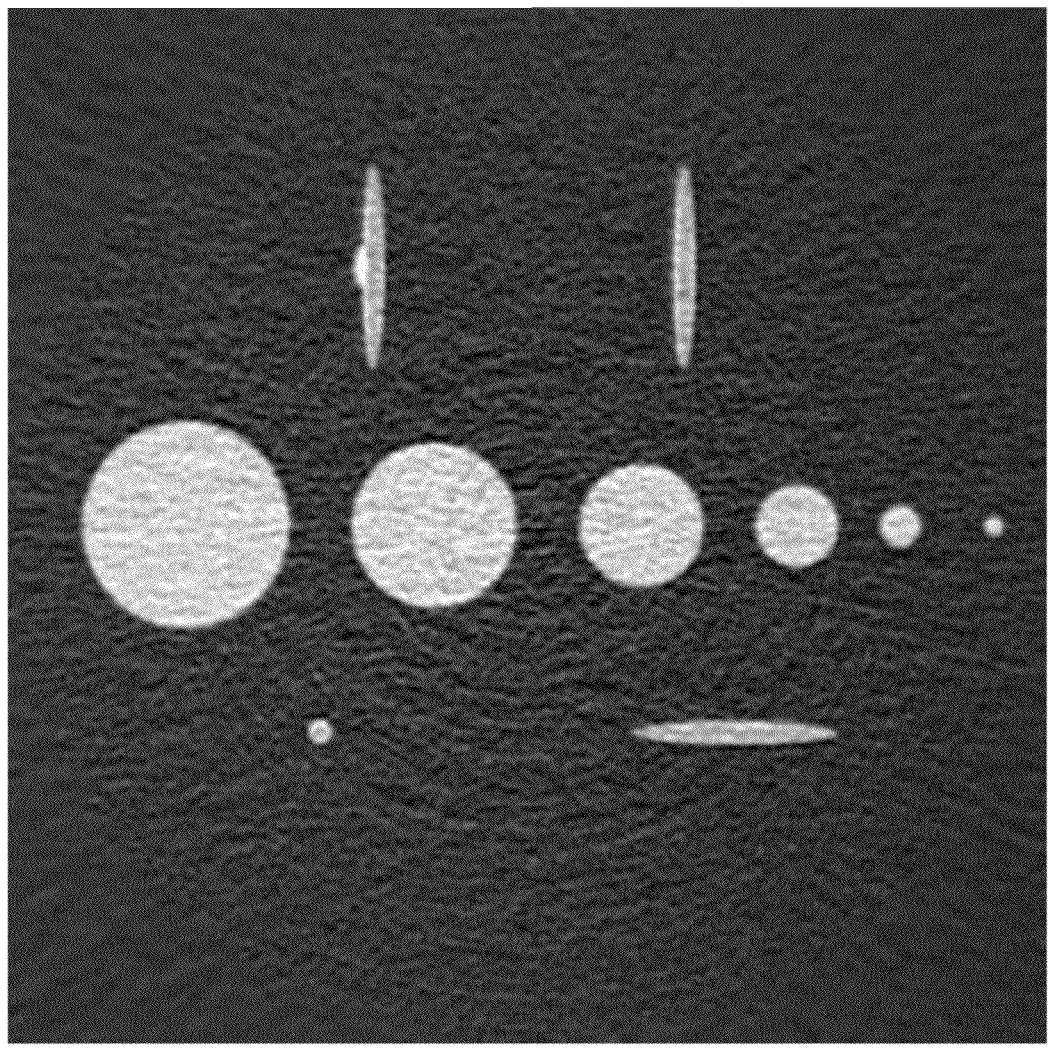
FIG. 8 is an illustration of the same slice as in FIG. 5 through the volume of $f_{h1}$ that was enhanced using an iterative-based enhancement algorithm.
Figure 9:
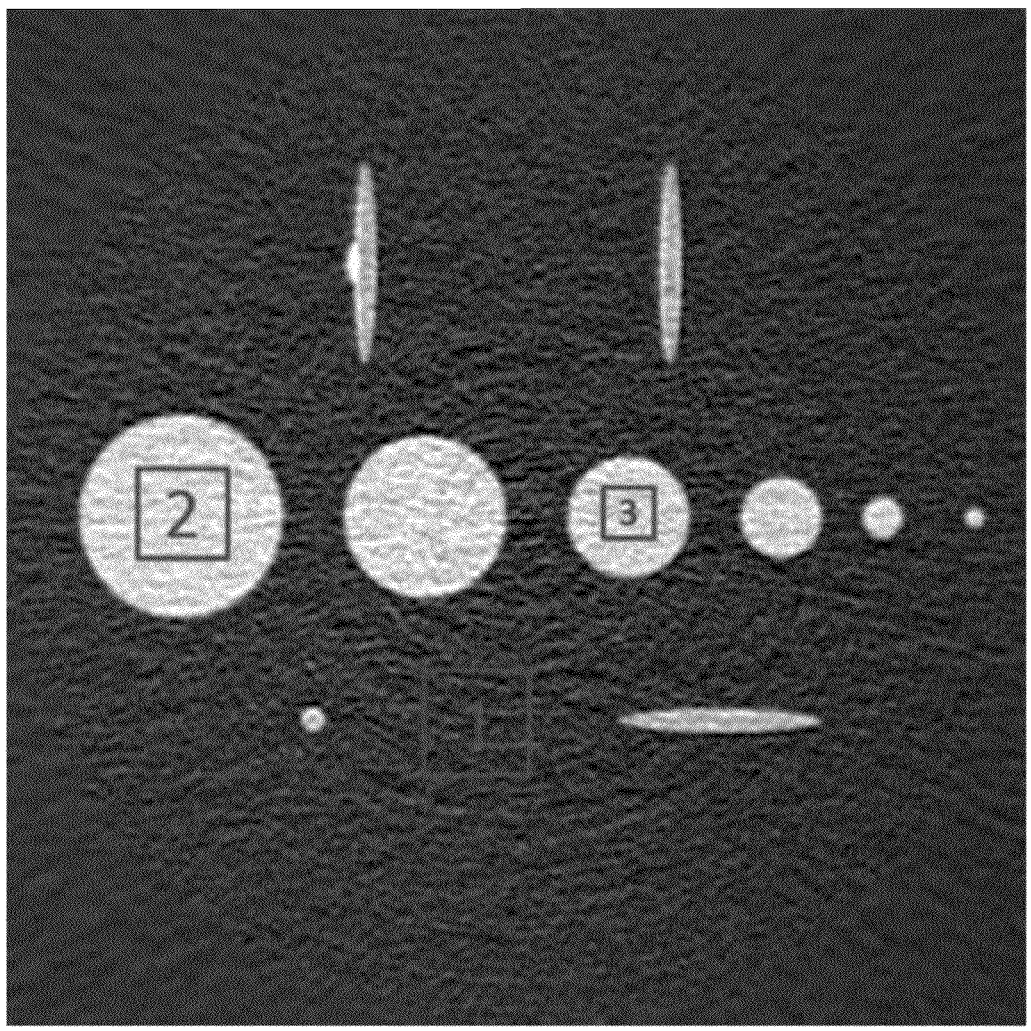
FIG. 9 is an illustration of the same image as in FIG. 8 with three rectangles used for computing average values of the attenuation coefficient in different parts of the phantom, including its background part (rectangle 1) and two embedded objects (rectangles 2 and 3), in accordance with an embodiment of the present invention.

In the exemplary embodiment, a bilateral filtration algorithm was used to filter the raw CB projection data to remove random and/or sensor noise. The reconstruction of the conventional image of the $f_c$ was performed by an iterative algorithm of D. Kim, S. Ramani, and J. A. Fessler, "Accelerating X-ray CT ordered subsets image reconstruction with Nesterov's first-order methods", Proceedings of The 12th International Meeting on Fully Three-Dimensional Image Reconstruction in Radiology and Nuclear Medicine, 2013, pp. 22-25, wherein the number of subsets was selected to be 10 and 120 sub-iterations (i.e., 12 full iterations) were specified. The reconstruction of the LT image $f_1$ was performed using variable filter length LT techniques, as previously described with reference to the variable filter length LT embodiment of the present invention, and the filter previously described in equation 1.3, with L=1. To compute the filtered LT image, $\bar{f}_1$, the high-pass filter co in (1.6) was chosen to be the identity minus a moving average over a cube of size 7×7×7 voxels. To calculate the first HLT image, $f_{h1}$, the value of "c" was chosen to be a constant equal to 2100. In the exemplary embodiment, iterative image enhancement based on Total Variation denoising was also applied, post-reconstruction An analysis of the results of the exemplary embodiment, show that HU values in the HLT reconstructed volume $f_{h1}$ are close to the true ones. FIGS. 5-8 show various intermediate functions constructed by the algorithm, and FIG. 9 shows the final HLT reconstruction. Simulated data with added Poisson random noise was used for the exemplary embodiment. The phantom is the superposition of ellipsoids of various constant attenuations.

Figure 5:
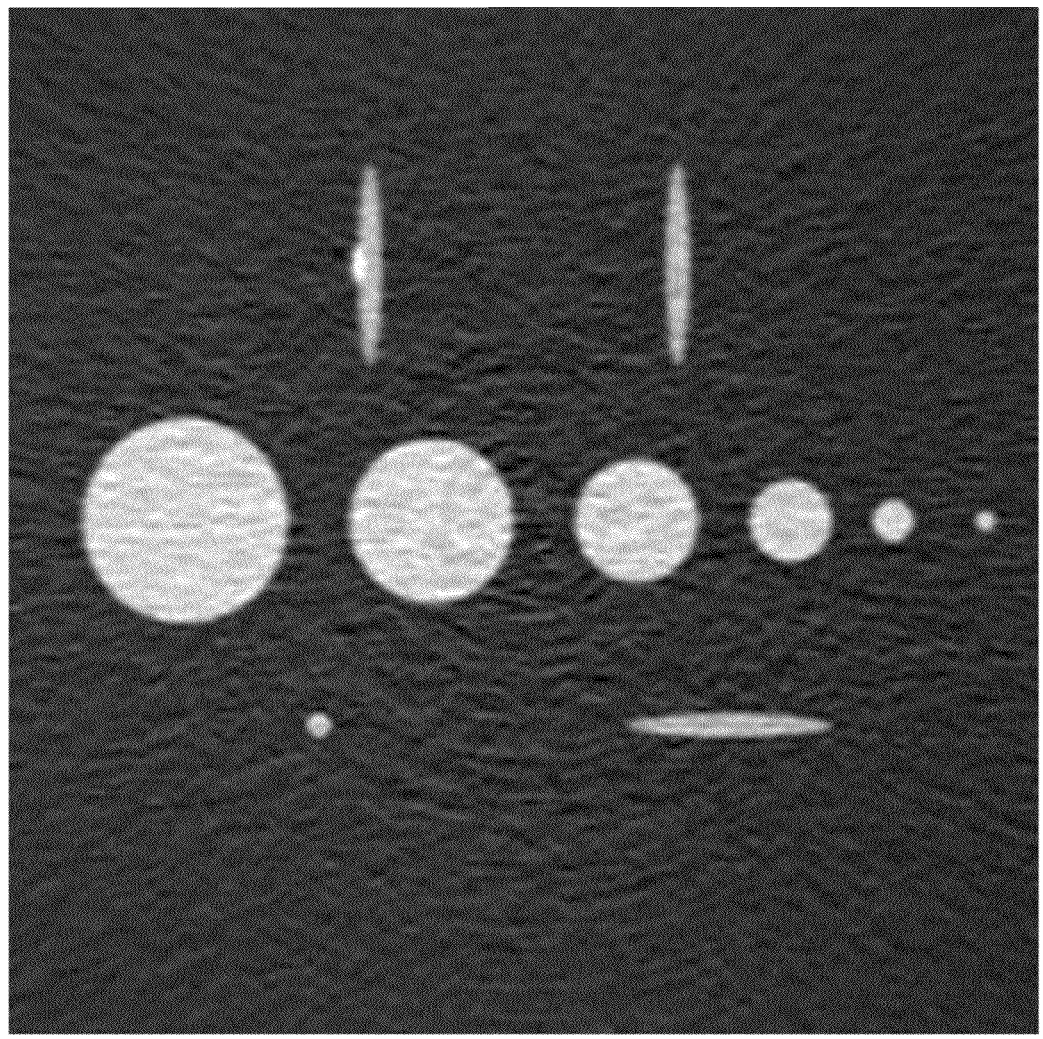
FIG. 5 is an illustration of a slice through the reconstructed volume of $f_c$ resulting from reconstruction in accordance with a conventional algorithm in accordance with an embodiment of the present invention.
Figure 6:
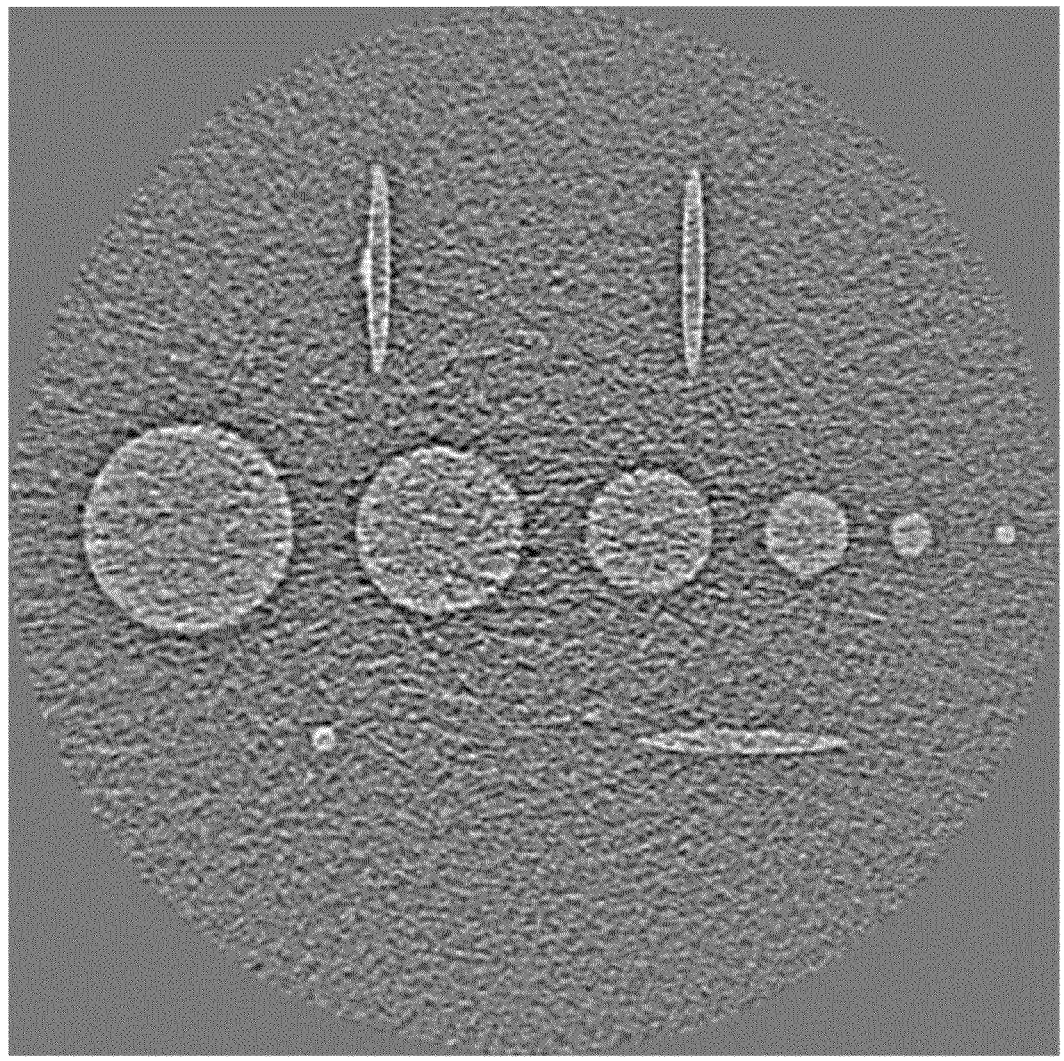
FIG. 6 is an illustration of the same slice as in FIG. 5 through the reconstructed volume of $f_l$ resulting from reconstruction in accordance with a LT algorithm in accordance with an embodiment of the present invention.

FIG. 5 illustrates a slice through the reconstructed volume of $f_c$ resulting from reconstruction in accordance with the exemplary embodiment. FIG. 6 is an illustration of the same slice as in FIG. 5 through the reconstructed volume of $f_1$ resulting from reconstruction in accordance with a LT algorithm in accordance with the exemplary embodiment. FIG. 7 is an illustration of the same slice as in FIG. 5 through the reconstructed volume of $f_{h1}$ resulting from the novel HLT reconstruction method in accordance with a conventional tomography algorithm and a LT algorithm in accordance with the exemplary embodiment. FIG. 8 is an illustration of the same slice as in FIG. 5 through the volume of $f_{h1}$ that was enhanced using an iterative based enhancement algorithm. FIG. 9 is an illustration of the same HLT image as in FIG. 8 with three rectangles used for computing average values of the attenuation coefficient in different parts of the phantom, including its background part (rectangle 1) and two embedded objects (rectangles 2 and 3), in accordance with an embodiment of the present invention.

The average value of the attenuation coefficient for each of the rectangles identified with reference to FIG. 9 are computed and the average computed values for the attenuation coefficients (HU values) are 1.023, 1.329, and 1.319 in squares #1, 2, and 3, respectively. Knowing that the correct HU values are 1.0, 1.3, and 1.3, respectively. It is shown that the estimated values of the attenuation coefficient derived from the final reconstructed volume $f_{h1}$ in accordance with the hybrid local tomography (HLT) reconstruction method of the present invention are approximately equal to the true expected values.

Figure 10:
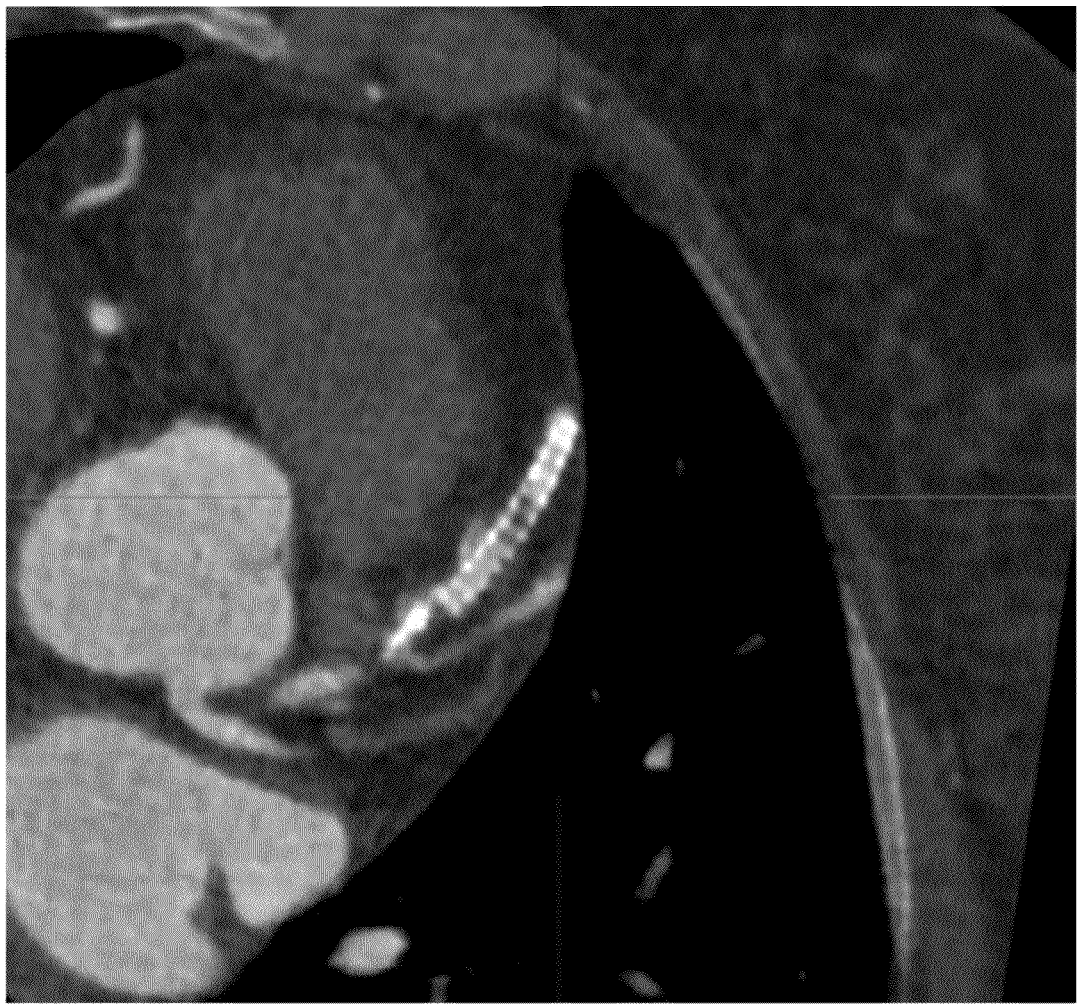
FIG. 10 is an illustration of a slice through the reconstructed volume of $f_{h1}$ for a clinical example of a coronary stent resulting from the novel HLT reconstruction in accordance with an embodiment of the present invention.

FIG. 10 is an illustration of a slice through the reconstructed volume of $f_{h1}$ for a clinical example of a coronary stent (the entire stent and its struts are well-seen in the middle part of FIG. 10) resulting from the novel HLT reconstruction workflow (#425 of FIG. 4) in accordance with an embodiment of the present invention. The raw CT data used to perform the HLT ($f_{h1}$) reconstruction was previously acquired by a top tier scanner during the normal course of medical care at the National Heart, Lung, and Blood Institute (NHLBI) of National Institutes of Health in Bethesda, Md.

Note that other embodiments of the present invention are possible, in which the low-pass filtered raw CT data-based conventional reconstruction $\bar{f}_c$ and/or the high-pass filtered raw CT data-based LT image $\bar{f}_1$ are computed not by applying an appropriate filter to an appropriate volume in the image domain, but by applying the appropriate processing steps in the CT data domain. In this embodiment in some cases no filtering in the image domain may be required.

HARDWARE AND SOFTWARE INFRASTRUCTURE EXAMPLES

The present invention may be embodied on various computing platforms that perform actions responsive to software-based instructions. The following provides an antecedent basis for the information technology that may be utilized to enable the invention.

The computer readable medium described in the claims below may be a computer readable signal data medium or a computer readable data storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires or wireless connection, a portable computer diskette or other data storage device, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, other data storage device, or any suitable combination of the foregoing. In the context of this document, a computer readable storage medium may be any tangible medium that can contain, or store a program for use by or in connection with an instruction execution system, apparatus, or device.

A computer readable signal data medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal data medium may be any computer readable medium that is not a computer readable storage medium and that can communicate, propagate, or transport a program for use by or in connection with an instruction execution system, apparatus, or device.

Program code embodied on a computer readable data medium may be transmitted using any appropriate medium, including but not limited to wireless, wire-line, optical fiber cable, radio frequency, etc., or any suitable combination of the foregoing. Computer program code for carrying out operations for aspects of the present invention may be written in any combination of one or more programming languages, including an object oriented programming language such as Java, C#, C++, Fortran, scripting languages, or the like and conventional procedural programming languages, such as the "C" programming language or similar programming languages.

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

GLOSSARY OF CLAIM TERMS

Back-projection updating: use of a backprojection algorithm for reconstruction of an image. Generally, backprojection refers to the step of using projection data for updating the image volume being reconstructed.

Computer: a general purpose device that can be programmed to carry out a set of arithmetic or logical operations.

Cone beam (CB) projection data: two-dimensional data provided by a detector array integral to a computed tomography (CT) imaging system.

Curvelets: a higher dimensional generalization of the wavelet transform designed to represent images at different scales and different angles.

Detector: a two-dimensional array detector having a plurality of rows and a plurality of columns.

Filtering: a mathematical process by which one-, two-, or higher-dimensional data arrays are transformed with the purpose of changing the frequency content of the said arrays. Those purposes may include, but are not limited to suppression of noise and smoothing, edge enhancement and resolution recovery.

High-pass filter: a filter that passes signals with a frequency higher than a certain cutoff frequency and attenuates signals with frequencies lower than the cutoff frequency.

Image reconstruction: creation of a two- or three-dimensional image from projection data.

Low-pass filter: a filter that passes signals with a frequency lower than a certain cutoff frequency and attenuates signals with frequencies higher than the cutoff frequency.

Ramp filter: a high pass filter, whose graph in the frequency domain looks like a linearly increasing ramp function. To avoid artifacts, at the highest frequencies the ramp filter may go to zero in a smooth fashion.

Region of Interest (ROI)—any subset inside the object being scanned, which can be strictly smaller than the object or can even coincide with the object itself.

Truncated CB data: CB data which is insufficient for theoretically exact reconstruction at a given point.

Wavelets: a class of functions, which is used to localize a given function both in space and scale.

Hounsfield Unit (HU): a way to characterize radiation attenuation in different tissues which measures radiodensity and is a quantitative scale.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A Hybrid Local Tomography (HLT) method for reconstructing an image of a region of interest (ROI) of an object, the image including values of the attenuation coefficient of the ROI, the method comprising:
   scanning an object to collect cone-beam (CB) projection data of the object, the CB projection data provided to a computer by at least one detector;
   computing a conventional image of a region of interest (ROI) using the CB projection data, the conventional image of the ROI comprising values of the attenuation coefficient of the ROI;
   computing a high-pass filtered LT image of the ROI using the CB projection data, the high-pass filtered LT image of the ROI comprising emphasized edges of the ROI;
   identifying a first balancing constant or function; and
   computing a summation of the conventional image of the ROI and a product of the first balancing constant or function and the high-pass filtered LT image of the ROI to reconstruct a first image of the ROI of the object, the first image of the ROI including the values of the attenuation coefficient of the ROI.

2. The method of claim 1, wherein computing a high-pass filtered LT image of the ROI further comprises, reconstructing a variable filter length LT image of the ROI using the CB projection data, and convolving the LT image in the image domain with a high-pass filtering kernel.

3. The method of claim 1, wherein computing a conventional image of the ROI further comprises computing a low-pass filtered conventional image of the ROI.

4. The method of claim 3, wherein computing a low-pass filtered conventional image of the ROI further comprises, reconstructing the conventional image of the ROI and convolving the conventional image in the image domain based upon a low-pass filtering kernel.

5. The method of claim 3, further comprising, identifying a second balancing constant or function.

6. The method of claim 5, further comprising, computing a summation of the low-pass filtered conventional image of the ROI and a product of the second balancing constant or function and the high-pass filtered LT image of the ROI to reconstruct a second image of the ROI of the object, the second image including the values of the attenuation coefficient of the ROI.

7. The method of claim 1, wherein the distribution of the attenuation coefficient of the conventional image is in Hounsfield Units (HU).

8. The method of claim 1, further comprising, performing filtration of the CB projection data to remove unwanted noise from the CB projection data.

9. The method of claim 1, wherein reconstructing a conventional image of the ROI using the CB projection data further comprises, reconstructing the conventional image of the ROI using an iterative-based algorithm.

10. The method of claim 1, wherein reconstructing a conventional image of the ROI using CB projection data further comprises, reconstructing the conventional image of the ROI using a filtered back projection (FBP)-based algorithm.

11. The method of claim 6, further comprising:
displaying the first image of the ROI of the object;
displaying the second image of the ROI of the object; and
comparing the image quality of the first image of the ROI to the image quality of the second image of the ROI to identify the image having the higher image quality.

12. The method of claim 1, wherein identifying a first balancing constant or function further comprises, executing a predetermined algorithm to automatically determine the first balancing constant or function during the reconstruction of the first image of the ROI.

13. The method of claim 1, wherein identifying a first balancing constant or function further comprises, estimating a plurality of possible first balancing constants or functions prior to the reconstruction of the first image and selecting an appropriate first balancing constant or function during the reconstruction of the first image of the ROI.

14. The method of claim 1, further comprising adjusting the first balancing constant or function during the reconstruction of the first image of the ROI.

15. The method of claim 5, wherein identifying a second balancing constant or function further comprises, executing a predetermined algorithm to automatically determine the second balancing constant or function during the reconstruction of the second image of the ROI.

16. The method of claim 5, wherein identifying a second balancing constant or function further comprises, estimating a plurality of possible second balancing constants or functions prior to the reconstruction of the second image and selecting an appropriate first balancing constant or function during the reconstruction of the second image of the ROI.

17. The method of claim 5, further comprising adjusting the second balancing constant or function during the reconstruction of the second image of the ROI.

18. The method of claim 2, wherein computing the variable filter length LT image of the ROI using the CB projection data, further comprises:
repeatedly loading and using additional CB projection data until reconstruction of the variable filter length LT image of the ROI is finished at all reconstruction points x;
wherein reconstruction of the variable filter length LT image of the ROI using the CB projection data comprises only using truncated CB projection data at one or more reconstruction points x inside the object, wherein the truncated CB projection data is defined as data which is insufficient for theoretically exact reconstruction at a point x;
wherein reconstruction of the variable filter length LT image of the ROI using the CB projection data further comprises:
filtering the truncated CB projection data; and
back-projection updating of the variable filter length LT image being reconstructed;
wherein filtering the truncated CB projection data uses a filter of a length longer than the length of a filter associated with computing a derivative, but shorter than the length of a filter associated with theoretically exact reconstruction (of infinite length or of length equal to a support of the object along the line of filtration);
wherein the variable filter length LT image reconstructed by repeatedly loading and using additional CB projection data is not intended to approximate a theoretically exact reconstruction, but allows differentiation of tissue types that comprise the object being scanned, and
wherein the computer does not process the CB projection data for the variable filter length LT image reconstruction using iterative steps, does not perform filling in of the missing data, and does not use wavelets and curvelets.

19. The method of claim 18, wherein the reconstruction points are confined to a region of interest (ROI) strictly in the interior of the object.

20. The method of claim 18, wherein filtering the truncated CB projection data uses a filter, which is different from a truncated version of a ramp filter.

21. The method of claim 20, wherein the filter is modified so that differentiation of materials that constitute the object using the reconstructed variable filter length LT image is improved.

22. The method of claim 20, wherein the filter is K(j) and the filter satisfies the equation $$\sum_{j=-n}^{n} K(j) = 0,$$

where n is the filter half-width.

23. The method of claim 18, further comprising, loading the CB projection data into a computer by denoting the CB projection data as $D_f(s,u,v)$, wherein CB projection corresponds to source position $y(s_k)$, and detector surface corresponding to the x-ray source located at $y(s_k)$ is denoted $DP(s_k)$.

24. The method of claim 18, wherein the filtering the truncated CB projection data further comprises, calculating filtered values according to:

$$g_1(s_k, i_c, i_r) = \sum_{j=-n}^{n} D_f(s_k, i_c - j, i_r) K(j),$$

where K(j) is the filter, n is the half-width of the filter, and $g_1(s_k,i_c,i_r)$ is the filtered data, $i_r$ is the index of a detector row, $i_c$ is the index of a detector column, and $D_f(s_k,i_c,i_r)$ is the CB projection data in the $(i_c,i_r)$ location on the detector.

25. The method of claim 18, wherein back-projection updating of the variable filter length LT image being reconstructed further comprises:
    fixing a reconstruction point x, which represents a point inside a patient where it is required to reconstruct the image;
    finding the projection z of x onto a detector $DP(s_k)$, with $(i_c^x, i_r^x)$ be the row- and column-coordinates of x̂ on the detector;
    if x̂ projects onto the detector, the filtered CB projection data affects the image at x, the method further comprises;
    identifying rows and columns on the detector that are close to the said projection x̂ to determine values of $g_1(s_k,i_c,i_r)$ for $(i_c,i_r)$ close to $(i_c^x,i_r^x)$;
    estimating value of $g_1(s_0,i_c^x,i_r^x)$ with interpolation from the said values of $g_1(s_0,i_c,i_r)$ for $(i_c,i_r)$ close to $(i_c^x,i_r^x)$;
    computing contribution from the said filtered CB projection data to the image being reconstructed at the point x by multiplying $g_1(s_k,i_c^x,i_r^x)$ by a weight function $w(s_k,x)$;
    adding the contribution to the image being reconstructed at the point x according to a pre-selected scheme;
    or, if x̂ projects outside the detector, then the filtered CB projection data is not used for image reconstruction at x, then fixing another reconstruction point x; and
    repeatedly fixing another different reconstruction point x until all reconstruction points have back-projection.

26. A Hybrid Local Tomography (HLT) system for reconstructing an image of a region of interest (ROI) of an object, the image including values of the attenuation coefficient of the ROI, the system comprising:
    a scanner comprising at least one detector, the scanner for scanning an object to collect cone-beam (CB) projection data of the object;
    a computer coupled to the scanner, the computer for receiving the CB projection data from the scanner and the computer configured for;
    computing a conventional image of a region of interest (ROI) using the CB projection data, the conventional image of the ROI comprising the distribution of the attenuation coefficient of the ROI;
    computing a high-pass filtered LT image of the ROI using the CB projection data, the high-pass filtered LT image of the ROI comprising emphasized edges of the ROI;
    identifying a first balancing constant or function; and
    computing a summation of the conventional image of the ROI and a product of the first balancing constant or function and the high-pass filtered LT image of the ROI to reconstruct a first image of the ROI of the object, the first image of the ROI including values of the attenuation coefficient of the ROI.

27. The method of claim 26, wherein computing a high-pass filtered LT image of the ROI further comprises, reconstructing a variable filter length LT image of the ROI using the CB projection data and convolving the variable filter length LT image in the image domain with a high-pass filtering kernel.

28. The system of claim 26, wherein computing a conventional image of the ROI further comprises, computing a low-pass filtered conventional image of the ROI.

29. The system of claim 28, wherein computing a low-pass filtered conventional image of the ROI further comprises, reconstructing the conventional image of the ROI and convolving the conventional image in the image domain based upon a low-pass filtering kernel.

30. The system of claim 26, further comprising, identifying a second balancing constant or function.

31. The system of claim 29, further comprising, computing a summation of the low-pass conventional image of the ROI and a product of the second balancing constant or function and the high-pass filtered LT image of the ROI to reconstruct a second image of the ROI of the object, the second image including the values of the attenuation coefficient of the ROI.

32. The system of claim 27, wherein to compute the variable filter length LT image of the ROI, the computer is further configured for:
    repeatedly loading and using additional CB projection data until reconstruction of the variable filter length LT image of the ROI is finished at all reconstruction points x;
    wherein reconstruction of the variable filter length LT image of the ROI using the CB projection data comprises only using truncated CB projection data at one or more reconstruction points x inside the object, wherein the truncated CB projection data is defined as data which is insufficient for theoretically exact reconstruction at a point x;
    wherein reconstruction of the variable filter length LT image of the ROI using the CB projection data further comprises:
        filtering the truncated CB projection data; and
        back-projection updating of the variable filter length LT image being reconstructed;
    wherein filtering the truncated CB projection data uses a filter of a length longer than the length of a filter associated with computing a derivative, but shorter than the length of a filter associated with theoretically exact reconstruction (of infinite length or of length equal to a support of the object along the line of filtration);
    wherein the variable filter length LT image reconstructed by repeatedly loading and using additional CB projection data is not intended to approximate a theoretically exact reconstruction, but allows differentiation of tissue types that comprise the object being scanned, and
    wherein the computer does not process the CB projection data for the variable filter length LT image reconstruction using iterative steps, does not perform filling in of the missing data, and does not use wavelets and curvelets.

33. A computer-readable non-transitory storage medium storing a program causing a computer program to execute a method for reconstructing a Hybrid Local Tomography (HLT) image from cone beam (CB) projection data, the method comprising:
    scanning an object to collect cone-beam (CB) projection data of the object, the CB projection data provided to a computer by at least one detector;
    computing a conventional image of a region of interest (ROI) using the CB projection data, the conventional image of the ROI comprising the distribution of the attenuation coefficient of the ROI;

computing a high-pass filtered LT image of the ROI using the CB projection data, the high-pass filtered LT image of the ROI comprising emphasized edges of the ROI;

identifying a first balancing constant or function; and computing a summation of the conventional image of the ROI and a product of the first balancing constant or function and the high-pass filtered LT image of the ROI to reconstruct a first image of the ROI of the object, the first image of the ROI including the distribution of the attenuation coefficient of the ROI.

34. The method of claim 33, wherein computing a high-pass filtered LT image of the ROI further comprises, reconstructing a variable filter length LT image of the ROI using the CB projection data and convolving the LT image in the image domain with a high-pass filtering kernel.

35. The computer program method of claim 33, wherein computing a conventional image of the ROI, further comprises, computing a low-pass filtered conventional image of the ROI.

36. The computer program method of claim 35, wherein computing a low-pass filtered conventional image of the ROI further comprises, reconstructing a conventional image of the ROI using the CB projection data and convolving the conventional image in the image domain based upon a low-pass filtering kernel.

37. The computer program method of claim 35, further comprising, identifying a second balancing constant or function.

38. The computer program method of claim 37, further comprising, computing a summation of the low-pass conventional image of the ROI and a product of the second balancing constant or function and the high-pass filtered LT image of the ROI to reconstruct a second image of the ROI of the object, the second image including the distribution of the attenuation coefficient of the ROI.

39. The computer program method of claim 34, wherein to compute the variable filter length LT image of the ROI, the computer is further configured for:

repeatedly loading and using additional CB projection data until reconstruction of the variable filter length LT image of the ROI is finished at all reconstruction points x;

wherein reconstruction of the variable filter length LT image of the ROI using the CB projection data comprises only using truncated CB projection data at one or more reconstruction points x inside the object, wherein the truncated CB projection data is defined as data which is insufficient for theoretically exact reconstruction at a point x;

wherein reconstruction of the variable filter length LT image of the ROI using the CB projection data further comprises:

filtering the truncated CB projection data; and back-projection updating of the variable filter length LT image being reconstructed;

wherein filtering the truncated CB projection data uses a filter of a length longer than the length of a filter associated with computing a derivative, but shorter than the length of a filter associated with theoretically exact reconstruction (of infinite length or of length equal to a support of the object along the line of filtration);

wherein the variable filter length LT image reconstructed by repeatedly loading and using additional CB projection data is not intended to approximate a theoretically exact reconstruction, but allows differentiation of tissue types that comprise the object being scanned, and wherein the computer does not process the CB projection data for the variable filter length LT image reconstruction using iterative steps, does not perform filling in of the missing data, and does not use wavelets and curvelets.

* * * * *

UNITED STATES PATENT AND TRADEMARK OFFICE
CERTIFICATE OF CORRECTION

| | | |
|---|---|---|
| PATENT NO. | : 9,042,626 B1 | Page 1 of 1 |
| APPLICATION NO. | : 14/557046 | |
| DATED | : May 26, 2015 | |
| INVENTOR(S) | : Alexander Katsevich et al. | |

It is certified that error appears in the above-identified patent and that said Letters Patent is hereby corrected as shown below:

In the Claims,

Column 17, Claim 25, Line 17 should read:

finding the projection $\hat{x}$ of $x$ onto a detector $DP(s_k)$, with

Signed and Sealed this
Twenty-ninth Day of September, 2015

Michelle K. Lee
*Director of the United States Patent and Trademark Office*